US006533718B1

(12) United States Patent
Ritchie et al.

(10) Patent No.: US 6,533,718 B1
(45) Date of Patent: Mar. 18, 2003

(54) SEX AID

(76) Inventors: Steven D. Ritchie, 368 Bay Plaza, Treasure Island, FL (US) 33706; Harlie David Reynard, 5054 John Pass Ave., Madera Beach, FL (US) 33708

( * ) Notice: Subject to any disclaimer, the term of this patent is extended or adjusted under 35 U.S.C. 154(b) by 0 days.

(21) Appl. No.: 09/893,481

(22) Filed: Jun. 29, 2001

(51) Int. Cl.$^{7}$ .................................................. A61F 5/00
(52) U.S. Cl. ........................................................ 600/38
(58) Field of Search ...................... 600/38–41; 601/135, 601/137

(56) References Cited

PUBLICATIONS

The Original Glass Dildo, twelve printed pages from www.theoriginalglassdildo.com including “who we are”, “The Spinner”, and “The Dialer” Dec. 1998(date provided in text.*

Thick Ribbed Juicer from www.naughtytoyz.com, two pages, Jun. 28, 2002.*

Twisterd, from www.atlglassworks.com, one page, Jun. 28, 2002.*

Good Vibrations, p. 33, Summer 1997.*

* cited by examiner

*Primary Examiner*—Samuel G. Gilbert

(57) ABSTRACT

A sexual aid comprising a cylindrical shaft is disclosed. The shaft has a length with a first end and a second end. A base is integrally formed in the first end of the shaft. A conical head may be provided on the second end of the shaft. The shaft, base and/or conical head are fabricated of a generally lubricous glass-based material containing an appreciable amount of an oxide of boron. A recess and a knob may be formed into the based.

5 Claims, 4 Drawing Sheets

FIG 1
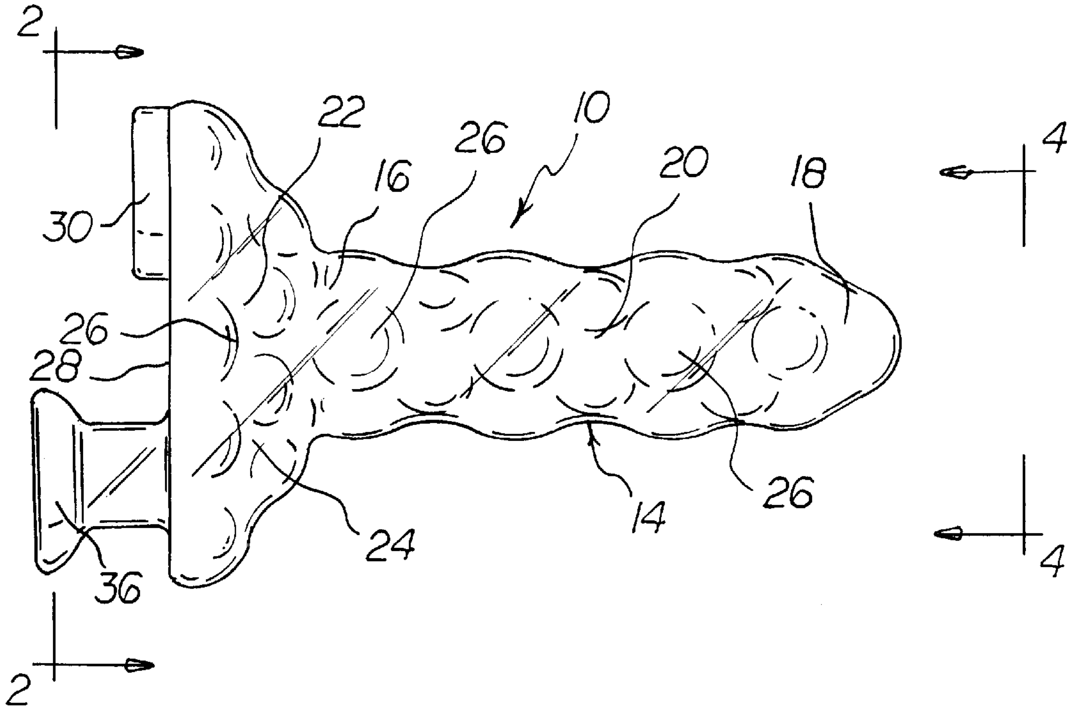
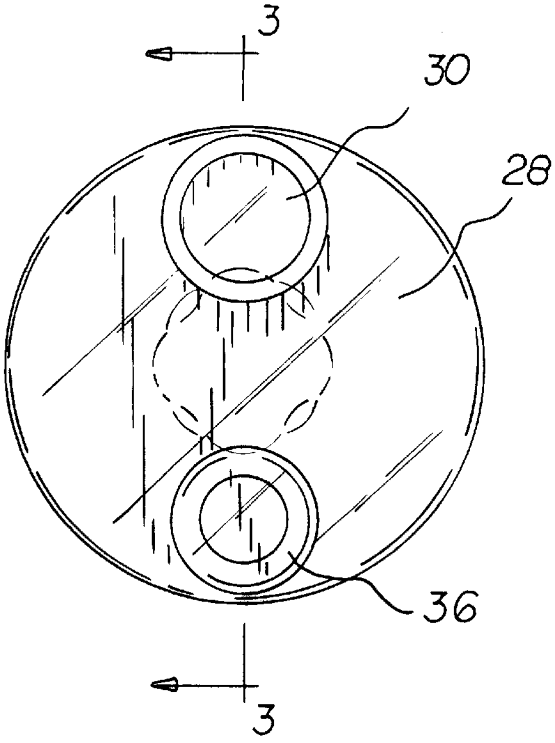
FIG 2

FIG 3
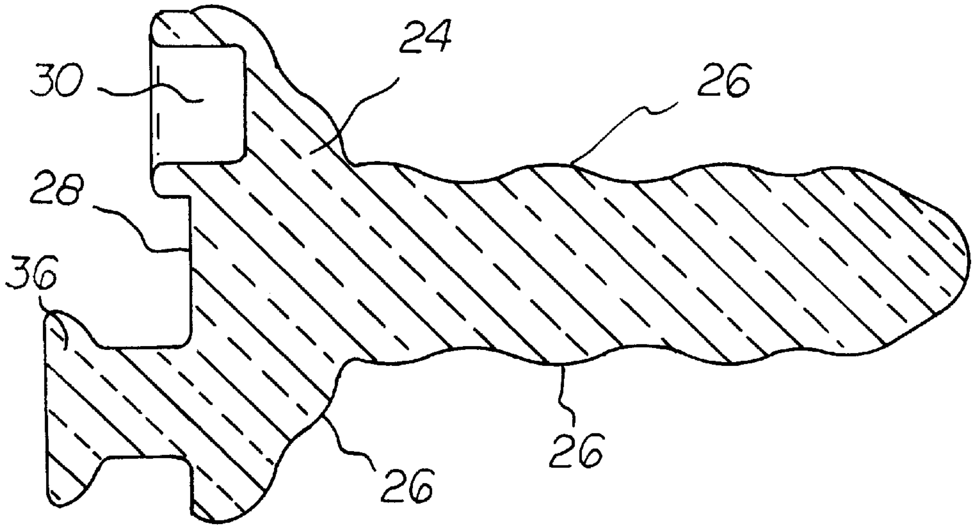
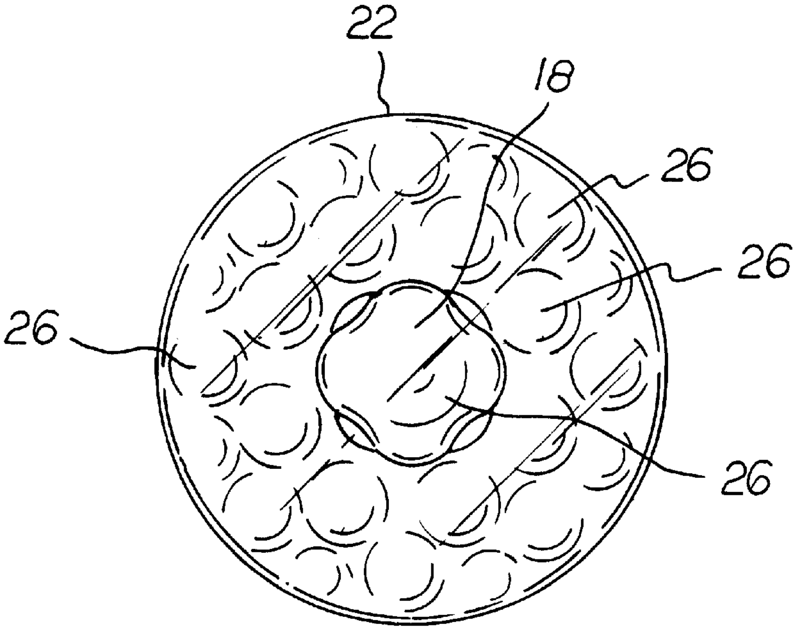
FIG 4

FIG 5
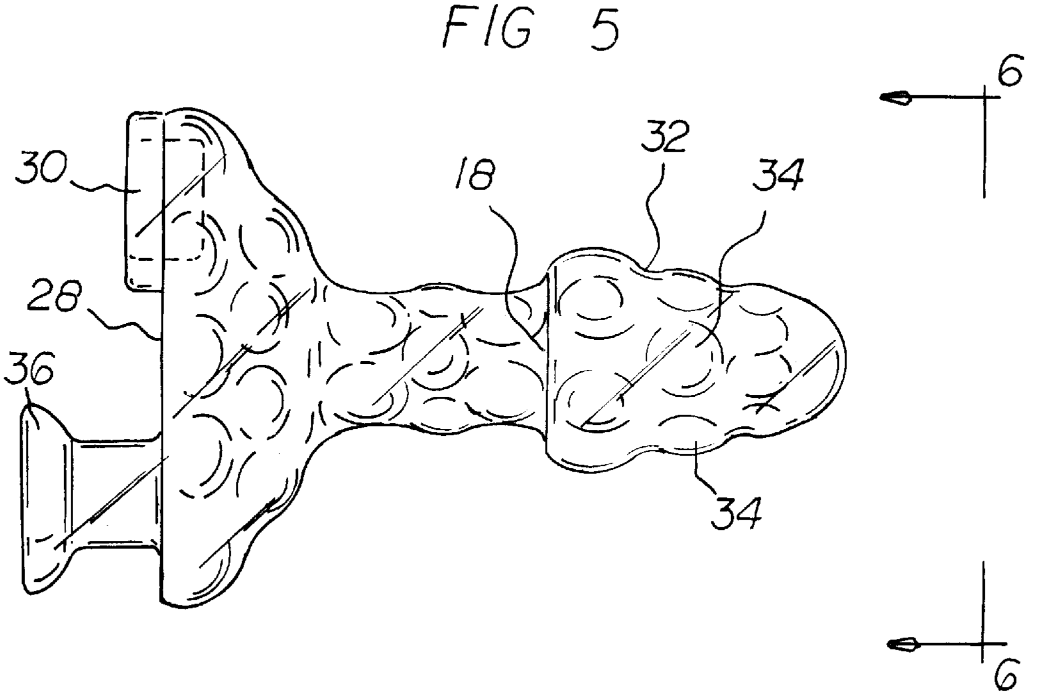
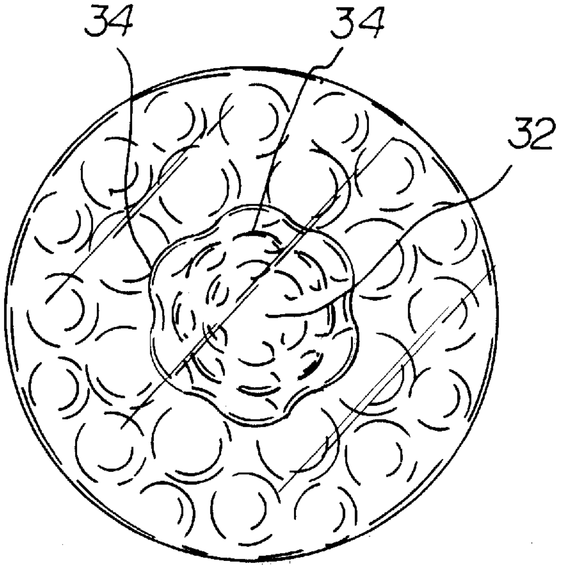
FIG 6

FIG 7
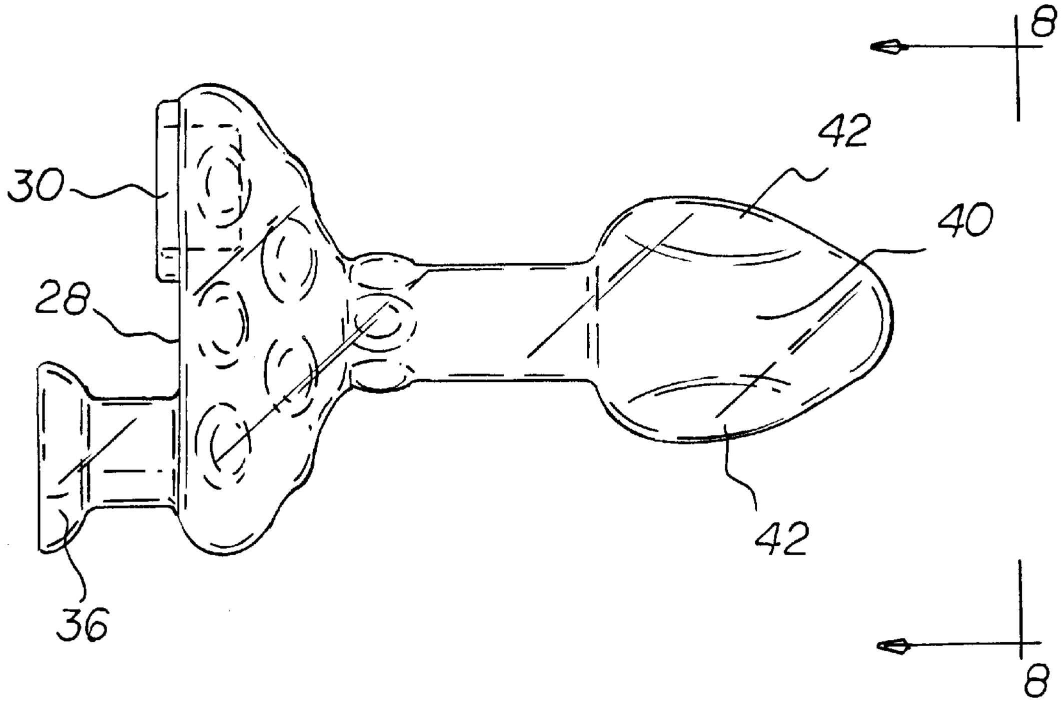
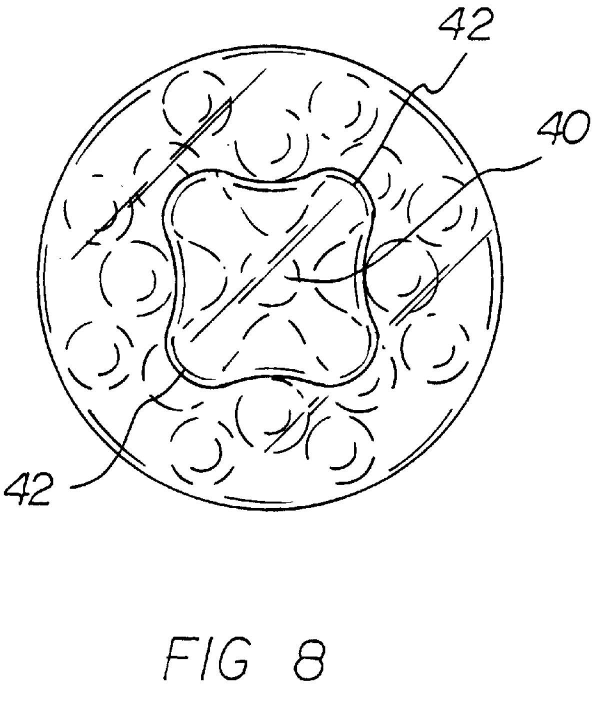
FIG 8

SEX AID

BACKGROUND OF THE INVENTION

1. Field of the Invention

The present invention relates to a new and improved sex aid and, more particularly, pertains to increasing stimulation during sex acts.

2. Description of the Prior Art

The use of sex aids of known designs and configurations is known in the prior art. More specifically, sex aids of known designs and configurations heretofore devised and utilized for the purpose of increasing sexual stimulation through known methods and apparatuses are known to consist basically of familiar, expected, and obvious structural configurations, notwithstanding the myriad of designs encompassed by the crowded prior art which has been developed for the fulfillment of countless objectives and requirements.

The prior art discloses a large number of sex aids of known designs and configurations. By way of example, U.S. Pat. No. DES. 272,649 to Bloch discloses a the ornamental design for an exerciser for orifice muscles.

In this respect, the sex aid according to the present invention substantially departs from the conventional concepts and designs of the prior art, and in doing so provides an apparatus primarily developed for the purpose of increasing stimulation during sex acts.

Therefore, it can be appreciated that there exists a continuing need for a new and improved sex aid which can be used for increasing stimulation during sex acts. In this regard, the present invention substantially fulfills this need.

SUMMARY OF THE INVENTION

In view of the foregoing disadvantages inherent in the known types of sex aids of known designs and configurations now present in the prior art, the present invention provides a new and improved sex aid. As such, the general purpose of the present invention, which will be described subsequently in greater detail, is to provide a new and improved sex aid and methods which have all the advantages of the prior art and none of the disadvantages.

To attain this, the present invention essentially comprises a new and improved sexual aid system for increasing stimulation during sex acts. The system includes a cylindrical shaft. The shaft has a length of between about 2½ and 3½ inches, preferably 3 inches. Further, the shaft has a first end and a second end and an intermediate cylindrical portion therebetween. The intermediate portion has a diameter of between about ⅜ and ⅝ inches, preferably ½ inches.

A base is integrally formed at the first end of the shaft. The base has a first curved face adjacent the first end of the shaft. Additionally, the base has a diameter of between about 2½ inches and 3½ inches, but preferably 3 inches. The base also includes a flat second surface opposite the first surface wherein the second surface may also include a recess and a knob formed integrally therein.

A plurality of raised nubs are formed on the surface of the shaft and the first surface of the base include. Alternately, a conical head may be integrally formed at the second end of the shaft. The conical head has a diameter of between about ¼ inches and 1¾ inches, preferably 1½ inches. The head further includes a plurality of ridge-like protrusions formed thereon.

The system is fabricated of a generally lubricous glass-based material containing an appreciable amount of an oxide of boron to render it lubricious and resistant to heat, chemicals and electricity.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sex aid which has all the advantages of the prior art sex aids of known designs and configurations and none of the disadvantages.

It is another object of the present invention to provide a new and improved sex aid which may be easily and efficiently manufactured and marketed.

It is a further object of the present invention to provide a new and improved sex aid which is of a durable and reliable construction.

It is yet a further object of the present invention to provide a new and improved sex aid which may be readily sterilized for improved sanitation.

An even further object of the present invention is to provide a new and improved sex aid which is susceptible of a low cost of manufacture with regard to both materials and labor, and which accordingly is then susceptible of low prices of sale to the consuming public, thereby making such a sex aid economically available to the buying public.

Even still another object of the present invention is to increase stimulation during sex acts.

Lastly, it is an object of the present invention to provide a sexual aid comprising a cylindrical shaft. The shaft has a length with a first end and a second end. A base is integrally formed in the first end of the shaft. A conical head may be provided on the second end of the shaft. The shaft, base and/or conical head are fabricated of a generally lubricous glass-based material containing an appreciable amount of an oxide of boron. A recess and a knob may be formed into the based.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of the first embodiment of the sex aid constructed in accordance with the principles of the present invention.

FIG. 2 is an end view taken along line 2—2 of FIG. 1.

FIG. 3 is a cross-sectional view taken along line 3—3 of FIG. 2.

FIG. 4 is an end view taken along line 4—4 of FIG. 1.

FIG. 5 is a side elevational view of an alternate embodiment of the invention.

FIG. 6 is an end view taken along line 6—6 of FIG. 5.

FIG. 7 is a side elevational view of a further alternate embodiment of the invention.

FIG. 8 is an end view taken along line 8—8 of FIG. 7.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved sex aid embodying the principles and concepts of the present invention and generally designated by the reference numeral 10 will be described.

The present invention, the new and improved sex aid, is a system 10 comprised of a plurality of components. Such components, in their broadest context, include a cylindrical shaft, a first end, and a second end. Each of the individual components is specifically configured and correlated one with respect to the other so as to attain the desired objectives.

The first component of the new and improved sexual aid system 10 for increasing stimulation during sex acts is a cylindrical shaft 14. The shaft has a length of between about 2½ and 3½ inches, preferably 3 inches. The shaft also has a first end 16 and a second end 18 and an intermediate cylindrical portion 20 therebetween. The intermediate portion of the shaft has a diameter of between about ⅜ and ⅝ inches, preferably ½ inches. In use the shaft is inserted into a woman's vagina for stimulation thereof.

The second component of the system is a base 22. The base is integrally formed at the first end of the shaft. The base further includes a first curved face or surface 24 adjacent the first end of the shaft. The base has diameter of between about 2½ inches and 3½ inches, preferably 3 inches. The base contacts the user's vaginal opening and clitoris when in use, preferably in a rotational manner.

All components of the sexual aid system, the shaft and base, are fabricated of a generally lubricous glass-based material. This glass-based material contains an appreciable amount of an oxide of boron to render it lubricious and resistant to heat, chemicals, electricity and bacterial absorption.

An alternate embodiment of the sex aid further includes raised nubs 26. The raised nubs are formed on the surface of the shaft and the first surface of the base. In use, the raised nubs provide for enhanced tissue and nerve stimulation of the clitoris and vaginal lips and walls when the invention comes in contact therewith. Further, the stimulating effect is enhanced when the invention is rotated within the user's vagina.

A further alternate embodiment of the sex aid includes a flat second surface 28 included in the base 22. The flat second surface is opposite the first surface. The flat surface includes a recess 30 formed integrally therein. The recess receives a user's finger for imparting a rotating motion to the device when placed within the user's vagina.

Yet another alternate embodiment of the sex aid includes a conical head 32. The conical head is integrally formed at the second end 18 of the shaft. The conical head has a diameter of between about ¼ inches and 1¾ inches, preferably 1½ inches. Further, the conical head includes a plurality of raised nubs 34 formed thereon. When placed within the user's vagina, the head and raised nubs provide deep stimulation for the user.

Another embodiment of the sex aid includes a knob 36 formed integrally with the flat second surface 28 of the base. The knob allows for an additional means to impart a rotational motion to the sex aid when placed within a user's vagina.

A final embodiment of the sex aid includes a conical head 40 integrally formed at the second end of the shaft. The conical head has a diameter of between about ¼ inches and 1¾ inches, preferably 1½ inches. Further, the conical head has a plurality of ridge-like protrusions 42 formed thereon. The protrusions give the conical head a somewhat squared cross-sectional shape. When placed within the user's vagina, the conical head and ridge-like protrusions provide enhanced deep stimulation for the user by deforming a user's tissues in an undulating manner.

The present invention is a group of stimulation devices designed for vaginal stimulation. Each of the embodiments has a unique grouping of raised nubs, ridge-like protrusions, knobs, or conical heads, and/or recesses for stimulation and handling of the devices.

Each of the embodiments of the present invention are hand-crafted from solid glass-based shafts. As such, the devices will stay slick for a long time without reapplying extra lubrication or rewetting. In addition, the devices will not hold odor. Each device is seamless, and created individually, one at a time. The devices are inspected carefully to insure perfect smoothness. The devices may be sterilized, washed in soap and water, wiped with alcohol or autoclaved. The devices may be used with water and oil-based lubricants. Unlike conventional water-based lubricants used to protect latex condoms which become sticky when used on rubber-like devices, the present invention provides smooth contact with rectal tissues. This arrangement of components and materials renders the present invention very suitable for mass production.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sexual aid system for increasing stimulation during sex acts comprising, in combination:

a cylindrical shaft having a central long axis with a length of between about 2½ and 3½ inches, the shaft having a first end and a second end and an intermediate cylindrical portion therebetween, the intermediate portion having a diameter of between about ⅜ and ⅝ inches;

a base integrally formed at the first end of the shaft, the base having a first curved face adjacent the first end of the shaft and having diameter of between about 2½ inches and 3½ inches, and a flat second surface opposite the first surface wherein the second surface includes a spin assisting component formed of a recess and a laterally displaced knob formed integrally therein, the recess and knob each having a short axis parallel with the long axis;

a plurality of raised nubs formed on the first surface of the base; and a conical head integrally formed at the second end of the shaft, the conical head having a diameter of between about ¼ inches and 1¾ inches, and having a plurality of ridge-like protrusions formed thereon, the shaft and base and conical head being fabricated of a generally lubricious glass-based material containing an appreciate amount of an oxide of boron to render it lubricious and resistant to heat, chemicals and electricity.

2. A sexual aid system for increasing stimulation during sex acts comprising, in combination:

a cylindrical shaft, the shaft having a first end and a second end and an intermediate cylindrical portion therebetween;

a base integrally formed at the first end of the shaft, the base having a first curved face adjacent the first end of the shaft and a flat second surface opposite the first surface wherein the second surface includes a spin assisting component formed integrally therewith;

a plurality of raised nubs formed on the first surface of the base;

a conical head is integrally formed at the second end of the shaft; and the shaft and base and conical head being fabricated of a generally lubricious glass-based material containing an appreciable amount of an oxide of boron to render it lubricious and resistant to heat, chemicals and electricity.

3. The system as set forth in claim 2 wherein the spin assisting component is a recess in a cylindrical configuration parallel with, but offset from, the cylindrical shaft.

4. The system as set forth in claim 2 wherein the spin assisting component is a knob in a cylindrical configuration parallel with, but offset from, the cylindrical shaft.

5. The system as set forth in claim 2 wherein the spin assisting component is a recess in a cylindrical configuration and a laterally displaced knob formed integrally therewith, the recess and knob each having a short axis parallel with the long axis.

* * * * *